United States Patent [19]

Goto et al.

[11] Patent Number: 5,187,161
[45] Date of Patent: Feb. 16, 1993

[54] P-AMINOPHENOL DERIVATIVES, AND PROCESSES FOR PRODUCTION OF AND USES FOR THE SAME

[75] Inventors: Kiyoto Goto; Kinji Hashimoto; Kenichi Kanai, all of Naruto, Japan

[73] Assignee: Otsuka Pharmaceutical Factory, Inc., Tokushima, Japan

[21] Appl. No.: 842,752

[22] Filed: Feb. 27, 1992

Related U.S. Application Data

[63] Continuation of Ser. No. 582,229, Oct. 3, 1990, abandoned.

[30] Foreign Application Priority Data

Feb. 23, 1989 [JP] Japan ..................... 1-44728

[51] Int. Cl.$^5$ ............... A61K 31/495; C07D 241/00; C07D 241/02; C07D 241/04
[52] U.S. Cl. .................... 514/255; 544/336; 544/407; 544/408; 544/409
[58] Field of Search .............. 544/336, 407, 408, 409; 514/255

[56] References Cited

U.S. PATENT DOCUMENTS 4,868,183 9/1989 Kanai et al. ............... 514/255
4,906,662 3/1990 Hashimoto et al. ........... 514/524

OTHER PUBLICATIONS

Derwent abstract for Japanese Unexamined Patent Publication 60-258,173, published Dec. 20, 1985.
Derwent abstract for Japanese Unexamined Patent Publication 62-123,180, published Jun. 4, 1987.
Derwent abstract for Japanese Unexamined Patent Publication 62-087,860, published Apr. 22, 1987.
Derwent abstract for Japanese Unexamined Patent Publication 63-115,860, published May 20, 1988.

Primary Examiner—Mukund J. Shah
Assistant Examiner—Matthew V. Grumbling
Attorney, Agent, or Firm—Armstrong, Westerman, Hattori, McLeland & Naughton

[57] ABSTRACT

A p-aminophenol derivative having anti-inflammatory activity, represented by the formula

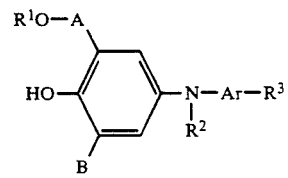

wherein each of $R^1$ and $R^2$ is independently a hydrogen atom or a $C_{1-6}$ acyl group; Ar is a pyrazine, pyrazine N-oxide, thiazole, benzene, pyridine, pyridazine, pyrimidine or triazine ring; $R^3$ is a hydrogen atom, a $C_{1-6}$ alkyl group, a $C_{1-6}$ alkoxy-carbonyl-$C_{1-6}$ alkyl group, a $C_{1-6}$ alkoxy group, a halogen atom or a carboxy-$C_{1-6}$ alkyl group; A is a $C_{1-6}$ alkylene group; and B is a $C_{1-6}$ alkyl group, or a salt thereof.

6 Claims, No Drawings

P-AMINOPHENOL DERIVATIVES, AND PROCESSES FOR PRODUCTION OF AND USES FOR THE SAME

This application is a continuation of application Ser. No. 582,229 filed Oct. 3, 1990, abandoned.

TECHNICAL FIELD

The present invention relates to pharmacologically active p-aminophenol derivatives, synthetic intermediates thereof, salts thereof, and processes for production thereof and pharmaceutical uses thereof.

PRIOR ART TECHNOLOGIES

The p-aminophenol derivatives, synthetic intermediates thereof and salts thereof, all of which are provided by the present invention, are novel compounds undisclosed in the literature.

Japanese Unexamined Patent Publications No.1-25756, No. 60-258173, No. 62-123180, No. 62-87580, and No. 63-115860 disclose various p-aminophenol derivatives which are somewhat related to the p-aminophenol derivatives of the present invention but none of the literature provides information at all on the p-aminophenol derivatives of the invention.

The object of the present invention is to provide novel p-aminophenol derivatives having valuable pharmacological activity, particularly antiinflammatory activity, a detailed discussion of which appears hereinafter, synthetic intermediates thereof, salts thereof, and processes for production of and pharmaceutical uses thereof.

DISCLOSURE OF THE INVENTION

In accordance with the present invention, there are provided p-aminophenol derivatives of the following formula (1), salts thereof, compounds of the following formula (1′), which are synthetic intermediates of said derivatives and salts, and salts thereof.

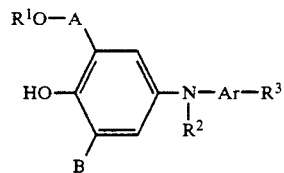
(1)

wherein $R^1$ and $R^2$ independently mean a hydrogen atom or a $C_{1-6}$ acyl group; Ar is a pyrazine ring, a pyrazine N-oxide ring, a thiazole ring, a benzene ring, a pyridine ring, a pyridazine ring, a pyrimidine ring or a triazine ring; $R^3$ is a hydrogen atom, a $C_{1-6}$ alkyl group, a $C_{1-6}$ alkoxycarbonyl-$C_{1-6}$ alkyl group, a $C_{1-6}$ alkoxy group, a halogen atom or a carboxy-$C_{1-6}$ alkyl group; A is a $C_{1-6}$ alkylene group; and B is a $C_{1-6}$ alkyl group.

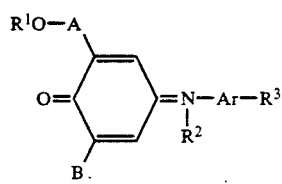
(1′)

wherein $R^1$ is a hydrogen atom or a $C_{1-6}$ acyl group; Ar is a pyrazine ring, a pyrazine N-oxide ring, a thiazole ring, a benzene ring, a pyridine ring, a pyridazine ring, a pyrimidine ring or a triazine ring; $R^3$ is a hydrogen atom, a $C_{1-6}$ alkyl group, a $C_{1-6}$ alkoxycarbonyl-$C_{1-6}$ alkyl group, a $C_{1-6}$ alkoxy group, a halogen atom or a carboxy-$C_{1-6}$ alkyl group; A is a $C_{1-6}$ alkylene group; and B is a $C_{1-6}$ alkyl group.

In this specification, Ar stands for a pyrazine N-oxide ring such as pyrazine 1-oxide-2-yl, pyrazine 1-oxide-3-yl, etc., a thiazole ring such as 2-thiazolyl, 4-thiazolyl, 5-thiazolyl, etc., a pyridine ring such as 2-pyridyl, 3-pyridyl, 4-pyridyl, etc., a pyridazine ring such as 3-pyridazinyl, 4-pyridazinyl, etc., a pyrimidine ring such as 2-pyrimidinyl, 4-pyrimidinyl, 5-pyrimidinyl, etc., or a triazine ring such as 1,2,4-triazin-3-yl, 1,2,4-triazin-5-yl, 1,2,4-triazin-6-yl, 1,3,5-triazin-2-yl, 1,2,3-triazin-4-yl, 1,2,3-triazin-5-yl, etc.

The $C_{1-6}$ acyl group is a straight-chain or branched acyl group of 1 to 6 carbon atoms, such as acetyl, propionyl, butyryl, isobutyryl, valeryl, isovaleryl, trimethylacetyl, hexanoyl and so on.

The $C_{1-6}$ alkyl group is a straight-chain or branched alkyl group of 1 to 6 carbon atoms, such as methyl, ethyl, propyl, isopropyl, butyl, isobutyl, tert-butyl, pentyl, hexyl and so on.

The $C_{1-6}$ alkoxy group is a straight-chain or branched alkoxy group of 1 to 6 carbon atoms, such as methoxy, ethoxy, propoxy, isopropoxy, butoxy, sec-butoxy, tert-butoxy, pentyloxy, hexyloxy and so on.

The $C_{1-6}$ alkoxy carbonyl-$C_{1-6}$ alkyl group is a straight-chain or branched alkoxycarbonylalkyl group of 1 to 6 carbon atoms, such as ethoxycarbonylmethyl, 2-methoxycarbonylethyl, 3-methoxycarbonylpropyl, 1-methyl-1-methoxycarbonylethyl, 4-methoxycarbonylbutyl, 5-methoxycarbonylpentyl, 6-methoxycarbonylhexyl, 1-ethoxycarbonylethyl, butoxycarbonylmethyl, 2-tert-butoxycarbonylethyl, pentyloxycarbonylmethyl, hexyloxycarbonylmethyl and so on.

The halogen atom includes fluorine, chlorine, bromine and iodine.

The carboxy-$C_{1-6}$ alkyl group is a straight-chain or branched carboxyalkyl group containing 1 to 6 carbon atoms in the alkyl moiety, such as carboxymethyl, 1-carboxyethyl, 2-carboxyethyl, 1-carboxy-1-methylethyl, 3-carboxypropyl, 4-carboxybutyl, 2-carboxy-1,1-dimethylethyl, 5-carboxypentyl, 6-carboxyhexyl and so on.

The $C_{1-6}$ alkylene group is a straight-chain or branched alkylene group of 1 to 6 carbon atoms, such as methylene, ethylene, trimethylene, 1-methymethylene, tetramethylene, 2-methyltrimethylene, pentamethylene, hexamethylene, 1,1-dimethylethylene and so on.

Of the compounds of formula (1) provided by the invention, the preferred compounds can be represented by the following formula (1A).

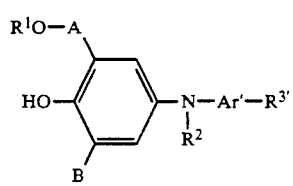
(1A)

wherein $R^1$, $R^2$, A and B are as defined hereinbefore; Ar′ is a pyrazine ring or a thiazole ring; and $R^{3\prime}$ is a hydrogen atom.

Typical examples of the above preferred compounds (1A) of the invention are as follows.

2-(1,1-Dimethylethyl)-6-(1,1-dimethyl-2-hydroxyethyl)-4-pyrazinylaminophenol 2-(1,1-Dimethylethyl)-6-(1,1-dimethyl-2-hydroxyethyl)-4-[N-(2-thiazolyl)amino]phenol 2-(2-Acetoxy-1,1-dimethylethyl)-6-(1,1-dimethylethyl)-4-[N-(2-thiazolyl)amino]phenol 2-(2-Acetoxy-1,1-dimethylethyl)-6-(1,1-dimethylethyl)-4-[N-acetyl-N-(2-thiazolyl)amino]phenol The compounds of formula (1) and salts thereof, which are provided by the present invention, have antiinflammatory, antirheumatic, antiasthmatic, antiallergy, antipyretic, analgesic, platelet aggregation-inhibiting, arteriosclerosis improving, antihyperlipidemic and other pharmacological activities and, as such, are of value as drugs for animals, particularly mammals, said drugs being antiinflammatory, antirheumatic, antiasthmatic, antiallergy, antipyretic, analgesic, antithrombotic and antiarteriosclerotic and/or antihyperlipidemic agents.

The 4-amino-2,5-cyclohexadien-1-one derivatives of the above general formula (1') and salts thereof are of value as synthetic intermediates for the production of the derivatives (1) of the invention.

The p-aminophenol derivatives of the invention can be produced by various processes. Some specific examples are shown below by reactions schemes.

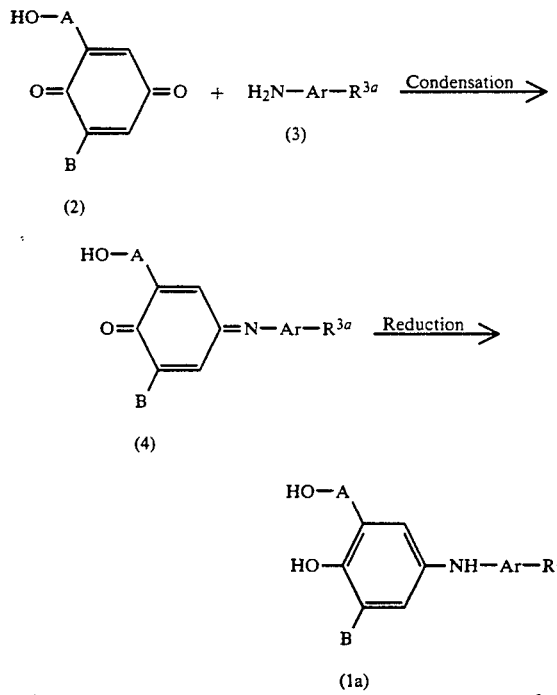

wherein Ar, A and B are as defined hereinbefore; $R^{3a}$ is a hydrogen atom, a $C_{1-6}$ alkyl group, a $C_{1-6}$ alkoxycarbonyl-$C_{1-6}$ alkyl group, a $C_{1-6}$ alkoxy group or a halogen atom.

In accordance with the above reaction scheme-1, the compound (1a) of the invention is produced by condensation of benzoquinone derivative (2) and aromatic amine derivative (3) and subsequent reduction reaction of the condensation product.

The benzoquinone derivative (2) and aromatic amine derivative (3) used as starting materials for the above reaction are both known compounds and some species of them are commercially available.

The above condensation reaction can be carried out by reacting benzoquinone derivative (2) with aromatic amine derivative (3), which doubles as an acid acceptor, in an inert organic solvent in the presence of a halide type Lewis acid, such as titanium tetrachloride, aluminum chloride, ferric chloride, stannic chloride, zinc chloride, etc., at temperature which may range from ambient temperature to about 120° C. The inert organic solvent mentioned above includes, among others, 1,2-dichloroethane, chloroform, benzene and toluene. This reaction system may include, as an acid acceptor, an inert organic base such as pyridine, triethylamine and so on. While the ratio of benzoquinone derivative (2) to aromatic amine derivative (3) is virtually optional, the former is used in a proportion of, generally, about 1 to 10 molar equivalents or, preferably, about 2 to 4 molar equivalents relative to the latter reactant. The above reaction using titanium tetrachloride can be carried out fundamentally in accordance with the method of Weingarten described in J. Org. Chem. 32, 3246, 1967, for instance. The compound (4) obtained in this manner may be optionally isolated and subject to the next reduction reaction but the reaction mixture as such may be used in the reduction reaction.

The reduction reaction of compound (4) following the above condensation reaction can be carried out using hydrogen gas in the presence of a catalyst such as palladium-carbon, platinum or the like to give the desired compound (1a) of the invention. As an alternative, the above reduction reaction can be performed by the method using sodium hydrosulfite, N,N-diethylhydroxylamine, or zinc and acetic acid.

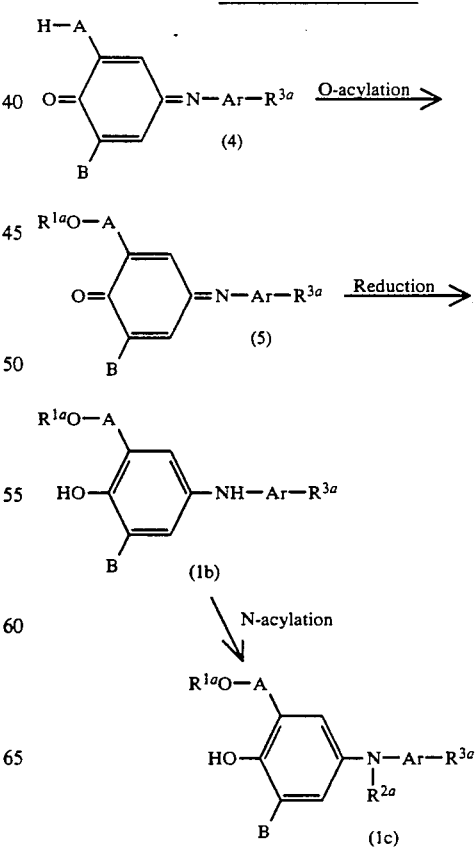

Reaction scheme-2 (continued)

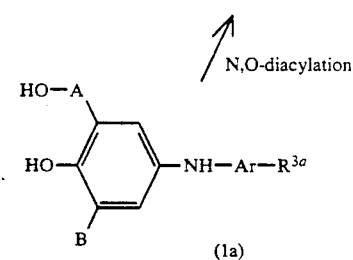

wherein Ar, A, B and $R^{3a}$ are as defined hereinbefore; $R^{1a}$ and $R^{2a}$ are either the same or different and each is an $C_{1-6}$ acyl group.

In accordance with reaction scheme-2, the compound (1b) of the invention can be produced via formation of compound (5) by O-acylation of compound (4) and subsequent reduction reaction of the O-acyl compound. The compound (1c) of the invention can be produced by N-acylation of compound 1b) or N,O-diacylation of compound (1a).

The O-acylation of compound (4) shown in the above reaction scheme-2 can be carried out by permitting a suitable acyclic $C_{1-6}$ alkanoic acid anhydride, such as acetic anhydride, propionic anhydride, etc., to act on the starting compound (4) either in the absence of a solvent or in the presence of a suitable solvent, such as pyridine, lutidine, collidin, acetic acid, etc., at a temperature which may range from ambient temperature to about 120° C. The ratio of the acid anhydride to compound (4) is virtually optional but is generally selected from within the range of about 1 to 10 molar equivalents.

The resulting compound (5) can be subjected to the next reduction reaction either after isolation from the reaction mixture or without isolation. This reduction reaction can be carried out under the same conditions as described for the reduction reaction according to reaction scheme-1.

The N-acylation of compound (1b) and N,O-diacylation of compound (1a) in accordance with reaction scheme-2 can be carried out using 2 to 20 molar equivalents of an acyclic $C_{1-6}$ alkanoic acid anhydride under the same conditions as described for the O-acylation of compound (4) to give the compound (1c) of the invention.

Reaction scheme-3

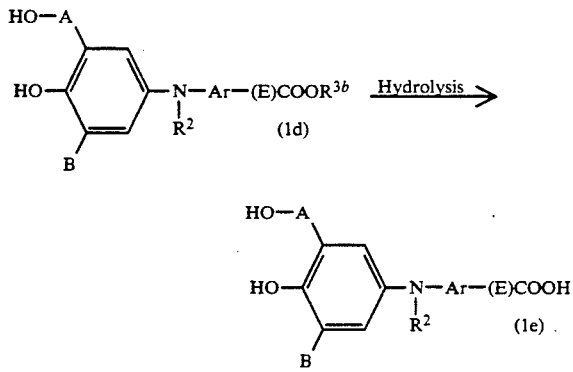

wherein Ar, A, B and $R^2$ are as defined hereinbefore; $R^{3b}$ is a $C_{1-6}$ alkyl group; and E is a $C_{1-6}$ alkylene group.

The hydrolysis reaction according to the above reaction scheme-3 can be carried out in an aqueous solvent consisting of water and an inert organic solvent, such as methanol, ethanol, tetrahydrofuran (THF), dioxane or the like, by treating compound (1d) with about 2 to 20 molar equivalents of sodium hydroxide, potassium hydroxide or the like in the presence or absence of about 1 to 20 molar equivalents of a reducing agent such as sodium hydrosulfite at a temperature between 0° C. and the boiling temperature of the solvent, preferably between 0° C. and ambient temperature. This hydrolysis reaction yields a compound (1e) of the invention.

The compounds of the invention obtained by the above reactions shown in the respective reaction schemes can be easily isolated and purified by the conventional procedures, among which are solvent extraction, recrystallization, column chromatography and so on.

The compound of the invention in general can be easily converted to pharmaceutically acceptable acid addition salts by addition reaction with the corresponding acid compounds. These acid addition salts have pharmacological activities similar to those of the free compounds. The invention covers these acid addition salts within its scope. The acid compounds capable of forming such acid addition salts include inorganic acids such as hydrochloric acid, sulfuric acid, phosphoric acid, hydrobromic acid, etc. and organic acids such as maleic acid, fumaric acid, malic acid, tartaric acid, citric acid, methanesulfonic acid, benzenesulfonic acid and so on. Furthermore, some of the compounds according to the invention can be reacted with basic compounds in the per se conventional manner to give pharmaceutically acceptable salts. Among such salts are alkali metal salts, e.g. lithium salts, sodium salts, potassium salts, etc., alkaline earth metal salts, e.g. calcium salts, magnesium salts, etc., and copper and other metal salts. These salts also have pharmacological activities similar to those of the free compound, and fall within the scope of the present invention.

The compound of the invention is generally used in the form of a preparation (pharmaceutical composition) containing an effective amount thereof. Such preparations are generally manufactured using diluents or excipients such as the conventional fillers, thinners, binders, humectants, disintegrating agents, surfactants, lubricants and so on.

Such preparations can be provided in various dosage forms according to the intended therapy, such as, typically, tablets, pills, powders, solutions, suspensions, emulsions, granules, capsules, suppositories, injections (solutions and suspensions), ointments and the like. The tablets can be manufactured using, as the carrier, excipients such as lactose, sucrose, sodium chloride, glucose, urea, starch, calcium carbonate, kaolin, crystalline cellulose, silica, etc., binders such as water, ethanol, propanol, simple syrup, glucose solutions, starch slurry, gelatin solutions, carboxymethyl cellulose, hydroxypropyl cellulose, methyl cellulose, potassium phosphate, polyvinylpyrrolidone, etc., disintegrating agents such as dried starch, sodium alginate, agar powder, laminaran powder, sodium bicarbonate, calcium carbonate, polyoxyethylene sorbitan-fatty acid esters, sodium laurylsulfate, stearyl monoglyceride, starch, lactose, etc., antidisintegrating agents such as sucrose, stearin, cacao butter, hydrogenated oils, ets., absorption promoters such as quaternary ammonium base, sodium lauryl sulfate, etc., humectants such as glycerol, starch, etc., adsorbents such as starch, lactose, kaolin, bentonite, colloidal silicic acid, etc., and lubricants such as purified talc, stearic acid salts, boric acid powder, polyethylene glycol, etc., and so forth. Furthermore, the tablets can be provided in various forms such as dragees, gelatin-coated tablets, enteric-coated tablets, film-coated tablets, double-layer tablets, multilayered tablets, and so on. The manufacture of pills can be carried out using, as carriers, excipients such as glucose, lactose, starch, cacao butter, hydrogenated vegetable oils, kaolin, talc, etc., binders such as gum arabic powder, tragacanth gum powder, gelatin, ethanol, etc. and disintegrating agents such as laminaran, agar, etc., to name but a few. The manufacture of suppositories can be performed using, as carriers, bases such as polyethylene glycol, cacao butter, higher alcohols, esters of higher alcohols, gelatin, semisynthetic glyceride and so on. For the manufacture of capsules, the compound of the invention can be mixed with carriers such as those mentioned above and filled into hard gelatin capsules, soft capsules and so on. In the manufacture of injections, the solution, emulsion and suspension used should be sterile and be preferably isotonic to the blood, and such injections can be manufactured using such diluents as water, ethanol, polyethylene glycol, propylene glycol, ethoxylated isostearyl alcohol, polyoxylated isostearyl alcohol, polyoxyethylene sorbitan fatty acid esters and so on. It should be understood that sodium chloride, glucose glycerol or the like may be incorporated in such pharmaceutical compositions in sufficient amounts to establish isotonicity and that the usual solubilizers or cosolvents, buffers, analgesic agents etc. may also be incorporated. Furthermore, colorants, preservatives, flavoring agents, sweetening agents and other corrigents as well as other drugs may be incorporated in the various pharmaceutical compositions mentioned hereinbefore. The manufacture of pastes, creams or gels can be performed using such diluents as white petrolatum, paraffin, glycerin, cellulose derivatives, polyethylene glycol, silicones, bentonite and so on.

The proportion of the compound of the invention in such a pharmaceutical composition of the invention is not critical but can be freely chosen from a broad range but is preferably in the range of 1 to 70 percent by weight for most purposes.

There is no particular limitation on the method for administration of the pharmaceutical composition of the invention. Thus, the method of administration can be selected according to dosage form, patient's age and sex, severity of disease and other factors. By way of example, the tablets, pills, solutions, suspensions, emulsions, granules and capsules can be administered by the oral route. The injections can be administered intravenously, either alone in combination with the usual infusions, such as glucose, amino acid and other infusions. If necessary, the injections are administered alone intramuscularly, intracutaneously, subcutaneously or intraperitoneally. The suppositories are directly administered into the rectum.

The dosage of the above pharmaceutical compositions is chosen according to the administration method, patient's age, sex and other background factors, severity of illness and so on. Generally speaking, the amount of the active compound of the invention should be about 0.5 to 500 mg/kg body weight/day. The pharmaceutical compositions of the invention can be administered in 2 to 4 divided doses a day.

EXAMPLES

To assist in a further understanding of the invention, examples of production of the starting compounds used in the production of compounds of the invention and examples of production of compounds of the invention are presented below as Reference Examples and Examples, respectively.

REFERENCE EXAMPLE 1

Production of 2-(1,1-dimethylethyl)-6-(1,1-dimethyl-2-hydroxyethyl)-1,4-benzoquinone

Step 1

In 1600 ml of acetic acid were dissolved 400 g of 2-(1,1-dimethylethyl)-4-methoxyphenol, 360 g of 40% glyoxal solution and 20 ml of 36% hydrochloric acid and the solution was heated at 120° C. with stirring for 4 hours. The reaction mixture was concentrated under reduced pressure and allowed to stand overnight. The resultant solid residue was washed with diethyl ether to give 105 g of 7-(1,1-dimethyethyl)-5-methoxy-2(3H)-benzofuranone as a light red solid.

The above filtrate was diluted with water and extracted with ethyl acetate and the organic layer was washed with saturated aqueous sodium hydrogen carbonate solution and saturated aqueous sodium chloride solution in that order, dried over magnesium sulfate and concentrated. The resultant crude product was crystallized from diethylether-hexane (1:1) to give a further crop (90 g) of 7-(1,1-dimethylethyl)-5-methoxy-2(3H)-benzofuranone as light red crystals.

m.p.: 117–118° C.

$^1$H-NMR (CDCl$_3$): δ1.37 (s, 9H), 3.69 (s, 2H), 3.79 (s, 3H), 6.68 (d, J=2.6Hz, 1H), 6.79 (d, J=2.6Hz, 1H).

Step 2

In 400 ml of N,N-dimethylformamide (DMF) was suspended 60.7 g of 60% sodium hydride followed by dropwise addition of a solution of 7-(1,1-dimethylethyl)-5-methoxy-2(3H)-benzofuranone (160 g) in DMF (1000 ml) at a temperature not exceeding 50° C. and the mixture was stirred for 30 minutes. Then, a solution of iodomethane (230 g) in DMF (100 ml) was added and the mixture was stirred at ambient temperature for 3 hours. The reaction mixture was poured in water and extracted with ethyl acetate. The organic layer was washed with saturated aqueous sodium chloride solution, dried over magnesium sulfate and concentrated. The resultant crude product was purified by silica gel column chromatography ( ethyl acetate-hexane =1:10) and washed with cold hexane to give 104 g of 3,3-dimethyl-7-(1,1-dimethylethyl)-5-methoxy-2(3H)-benzofuranone as a light yellow solid.

m.p.: 63.5-64.5 ° C.

$^1$H-NMR (CDCl$_3$) 1.39 (s, 9H), 1.49 (s, 6H), 3.81 (s, 3H), 6.59 (d, J=2.6Hz, 1H), 6.77 (d, J=2.6Hz, 1H).

Step 3

In 500 ml of diethyl ether was suspended 18 g of lithium aluminum hydride followed by addition of a solution of 3,3-dimethyl-7-(1,1-dimethylethyl)-5-methoxy-2(3H)-benzofuranone (104 g) in diethyl ether (400 ml) over a period of 1 hour with stirring at ambient temperature. The mixture was further stirred at ambient temperature for 1 hour. The reaction mixture was held under cooling in an ice bath and 60 ml of ethyl acetate, 100 ml of water and 900 ml of 10% hydrochloric acid were successively added. After phase separation, the aqueous layer was extracted with ethyl acetate and the organic layers were pooled, washed with saturated aqueous, sodium chloride solution, dried over magnesium sulfate and concentrated. The resultant crude product was crystallized from hexane to give 100 g of 2-(1,1-dimethylethyl)-6-(1,1-dimethyl-2-hydroxyethyl)-4-methoxyphenol as colorless crystals.

m.p.: 102.5–103.5 °C.

$^1$H-NMR (CDCl$_3$): $\delta$1.42 (s, 9H), 1.44 (s, 6H), 2.56 (t, J=4.3Hz,1H), 3.77 (s, 3H), 3.80 (d, J=4.3Hz, 2H), 6.71 (d, J=3.0Hz, 1H), 6.81 (d, J=3.0Hz, 1H), 8.74 (s, 1H).

Step 4

In a mixture of acetonitrile (275 ml) and water (165 ml) was dissolved 55 g of 2-(1,1-dimethylethyl)-6-(1,1-dimethyl-2-hydroxyethyl)-4-methoxyphenol, and under cooling in an ice bath, a solution of cerium (IV) diammonium nitrate (297 g) in 50% aqueous acetonitrile (440 ml) was added over a period of 10 minutes. The reaction mixture was stirred for 30 minutes, after which it was poured in water and extracted with ethyl acetate. The organic layer was washed with saturated aqueous sodium chloride solution, dried over magnesium sulfate and concentrated. The resultant crude product was crystallized from hexane to give 49 g of the desired compound as yellow crystals.

m.p.: 92–94 °C.

$^1$H-NMR (CDCl$_3$): $\delta$1.26 (s, 6H), 1.28 (s 9H), 1.81 (t, J=5.6Hz, 1H), 3.80 (d, J=5.6Hz, 2H), 6.53 (d, J=2.6Hz, 1H), 6.58 (d, J=2.6Hz, 1H).

EXAMPLE 1

Production of 2-(1,1-dimethylethyl)-6-(1,1-dimethyl-2-hydroxyethyl)-4-pyrazinylaminophenol [Compound 1]

Step 1

In 800 ml of dichloroethane was dissolved 13.4 g of pyridine followed by addition of 8.1 g of titanium tetrachloride. The mixture was refluxed for 15 minutes. Then, 10.0 g of 2-(1,1-dimethyethyl)-6-(1,1-dimethyl-2-hydroxyethyl)-1,4-benzoquinine and 12.1 g of aminopyrazine were added and the mixture was heated at 85° C. with stirring for 15 minutes. After cooling to ambient temperature, the reaction mixture was filtered through Celite and insolubles were washed with chloroform. The filtrate was washed with saturated aqueous sodium chloride solution, dried over magnesium sulfate and concentrated. The resultant crude product was purified by silica gel column chromatograpy (chloroform-ethyl acetate=6:1→3:1) to give 8.3 g of 2-(1,1-dimethylethyl)-6-(1,1-dimethyl-2-hydroxyethyl)-4-pyrazinylimino-2,5-cyclohexadien-1-one [Compound 1a] as a light red solid.

Furthermore, 3.7 g of 2-(1,1-dimethylethyl)-6-(1,1-dimethyl-2-hydroxyethyl)-1,4-benzoquinone was recovered.

The structure and physical properties of the product compound (m.p. and $^1$H-NMR data) are shown in Table 1.

Step 2

In 450 ml of ethyl acetate was dissolved 2.5 g of Compound 1a followed by addition of 0.30 g of 10% palladium-carbon as a catalyst. After purging the atmosphere in the reaction vessel with hydrogen gas, the reaction mixture was stirred at ambient temperature. After 180 ml of hydrogen had been consumed, the reaction mixture was filtered through Celite to remove the catalyst and the filtrate was washed with ethyl acetate and concentrated under reduced pressure. The crude product thus obtained was washed with diethyl ether to give 2.3 g of the desired compound as a colorless solid. The structure and physical properties of the product compound are shown in Table 2.

2-11

Production of Compound 2 through Compound 11

In the same manner as Step 1 of Example 1, Compound 2a to Compound 11a were respectively produced from 2-(1,1-dimethylethyl)-6-(1,1-dimethy-2-hydroxyethyl)-1,4-benzoquinone and 3-aminopyrazine 1-oxide, 2-aminothiazole, 2-amino-4-methylthiazole, ethyl 2-amino-4-thiazolylacetate, aniline, 4-fluoroaniline, 3-aminopyridine, 3-amino-6-methoxypyrazine, 2-aminopyrimidine or 3-amino-1,2,4-triazine. The structures and physical properties of the product compounds are shown in Table 1.

Then, from the respective compounds prepared as above, compounds of the invention (Compound 2 to Compound 11) were produced in the same manner as Step 2 of Example 1. The structures and physical properties of these compounds are shown in Table 2.

EXAMPLE 12

Production of 2-(2-acetoxy-1,1-dimethylethyl)-6-(1,1-dimethylethyl)-4-pyrazinylaminophenol [Compound 12]

Step 1

A mixture consisting of 2.2 g of Compound 1a (prepared in accordance with Step 1 of Example 1), 1.7 ml of acetic anhydride and 50 ml of pyridine was stirred at ambient temperature for 8 hours. The reaction mixture was then poured in ice-water and extracted with ethyl acetate. The organic layer was washed with saturated aqueous sodium chloride solution, dried over magnesium sulfate, and concentrated. The resultant crude product was purified by silica gel column chromatography (diethyl etherhexane=1:3→1:2) to give 1.6 g of 2-(2-acetoxy-1,1-dimethyl)-6-(1,1-dimethylethyl)-4-pyrazinylimino-2,5-cyclohexadien-1-one [Compound 12a] as a red oil. The structure and physical properties of this product compound are shown in Table 1.

Step 2

In the same manner as step 2 of Example 1, Compound 12a was hydrogenated in the presence of palladium-carbon to give the corresponding compound of the invention. The structure and physical properties of this product compound are shown in Table 2.

EXAMPLE 13

Production of 2-(2-acetoxy-1,1-dimethylethyl)-6-(1,1-dimethylethyl)-4-(2-thiazolylamino)phenol [Compound 13]

Step 1

In the same manner as Step 1 of Example 12, the desired compound [Compound 13a]was produced from Compound 3a (prepared in Step 1 of Example 3) and acetic anhydride. The structure and physical properties of this product compound are shown in Table 1.

Step 2

In 50 ml of THF was dissolved 1.3 g of Compound 13a followed by addition of a solution of sodium hydrosulfite (6.5 g) in water (150 ml). The mixture was stirred at ambient temperature for 10 minutes, after which it was extracted with ethyl acetate. The organic layer was washed with saturated aqueous sodium chloride solution, dried over magnesium sulfate, and concentrated. The resultant crude product was washed with diethyl etherhexane to give 1.0 g of the desired compound as a colorless solid. The structure and physical properties of this product compound are shown in Table 2.

EXAMPLE 14

Production of 2-(2-acetoxy-1,1-dimethylethyl)-6-(1,1-dimethylethyl)-4-[N-acetyl-N-(2-thiazolyl)amino]phenol [Compound 14]

A mixture consisting of 0.50 g of Compound 13 (prepared in Example 13) and 6 ml of acetic anhydride was heated at 100° C. for 1 hour. The reaction mixture was then cooled to ambient temperature and concentrated. The resulting crude product was purified by silica gel column chromatography (diethyl ether-hexane=1:2) to give 0.50 g of the desired compound as a colorless solid. The structure and physical properties of this product compound are shown in Table 2.

EXAMPLE 15

Production of 2-[3-(1,1-dimethylethyl)-5-(1,1-dimethyl-2-hydroxyethyl)-4-hydroxyphenylamino]-4-thiazolylacetic acid [Compound 15]

In a mixture of THF (40 ml) and ethanol (80 ml) was dissolved 3.2 g of compound 5 (prepared in Example 5). At ambient temperature, a solution of sodium hydrosulfite (5 g) in water (50 ml) and, then, 30 ml of 2N aqueous sodium hydroxide solution were added and the mixture was stirred for 1 hour. The reaction mixture was ice-cooled, treated with 50 ml of 1N hydrochloric acid and extracted with methylene chloride. The organic layer was washed with saturated aqueous sodium chloride solution, dried over magnesium sulfate and concentrated at about 0° C. The resultant crude product was crystallized from methylene chloride and washed with diethyl ether to give 0.80 g of the desired compound as colorless crystals. The structure and physical properties of this product compound are shown in Table 2.

TABLE 1

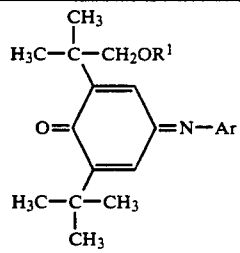

(About 1:1 mixture of syn-isomer and anti-isomer)

[Compound 1a]
Structure:

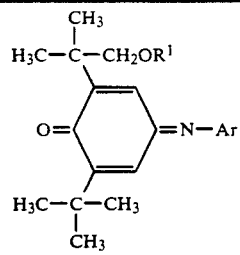

(About 1:1 mixture of syn-isomer and anti-isomer)

Ar = 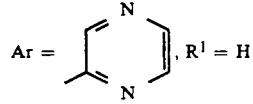, $R^1$ = H

Melting point: 100-103.5° C.
$^1$H-NMR (CDCl$_3$): δ
1.17(s, 6H), 1.21(s, 9H), 1.31(s, 6H)
1.33(s, 9H), 2.41(broad, 2H)
3.73(s, 2H), 3.81(s, 2H)
6.91(d, J=2.5Hz, 1H)
6.97(d, J=2.5Hz, 1H)
7.06(d, J=2.5Hz, 1H)
7.11(d, J=2.5Hz, 1H), 8.4~8.5(m, 6H)
[Compound 2a]
Structure:

Ar = 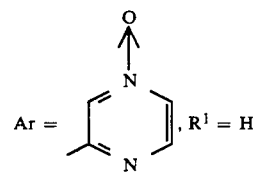, $R^1$ = H

Melting point: 117-119.5° C.
$^1$H-NMR (CDCl$_3$): δ
1.18(s, 6H), 1.21(s, 9H), 1.29(s, 6H)
1.32(s, 9H), 2.63(broad, 1H)
3.11(broad, 1H), 3.72(s, 2H)
3.80(s, 2H), 6.84(d, J=2.7Hz, 1H)
6.90(d, J=2.7Hz, 1H)
6.98(d, J=2.7Hz, 1H)
7.04(d, J=2.7Hz, 1H)
7.9-8.0(m, 4H), 8.33(d, J=1.5Hz, 1H)
8.34(d, J=1.5Hz, 1H)
[Compound 3a]
Structure:

Ar = 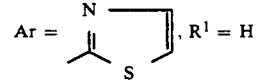, $R^1$ = H

Melting point: 80-83° C.
$^1$H-NMR (CDCl$_3$): δ
1.27(s, 6H), 1.30(s, 15H)
1.32(s, 9H), 1.68(broads, 1H)
2.31(broad, 1H), 3.78(s, 2H)
3.79(s, 2H), 7.01(d, J=2.6Hz, 1H)
7.05(d, J=2.6Hz, 1H)
7.42(d, J=1.6Hz, 1H)
7.43(d, J=1.6Hz, 1H)
7.79(d, J=1.6Hz, 1H)
7.81(d, J=1.6Hz, 1H)
8.05(d, J=2.6Hz, 1H)
8.08(d, J=2.6Hz, 1H)
[Compound 4a]
Structure:

Ar = 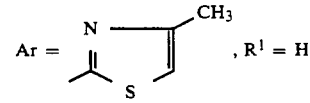, $R^1$ = H

TABLE 1-continued

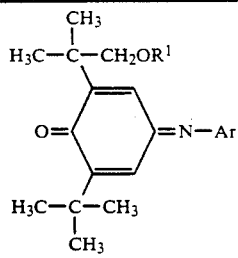

(About 1:1 mixture of syn-isomer and anti-isomer)

Not isolated
[Compound 5a]
Structure:

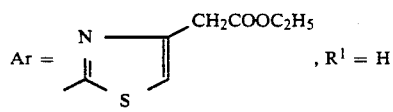

Properties: Oily product
$^1$H-NMR (CDCl$_3$): δ
1.2–1.4(m, 36H), 2.28(broad, 1H)
2.44(broad, 1H), 3.78(m, 4H)
3.81(t, J=0.8Hz, 4H)
4.1–4.3(m, 4H), 6.99(d, J=2.5Hz, 1H)
7.03(d, J=2.5Hz, 1H)
7.28(d, J=0.8Hz, 1H)
7.30(d, J=0.8Hz, 1H)
8.07(d, J=2.5Hz, 1H)
8.14(d, J=2.5Hz, 1H)
[Compound 6a]
Structure:

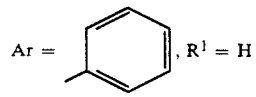

Melting point: 113–115° C.
$^1$H-NMR (CDCl$_3$): δ
1.14(s, 6H), 1.19(s, 9H), 1.31(s, 6H)
1.33(s, 9H), 2.25(t, J=5.8Hz, 1H)
2.35(t, J=5.8Hz, 1H)
3.72(d, J=5.8Hz, 2H)
3.81(d, J=5.8Hz, 2H), 6.8–6.9(m, 6H)
7.08(d, J=2.5Hz, 1H)
7.12(d, J=2.5Hz, 1H)
7.18–7.30(m, 2H), 7.3–7.5(m, 4H)
[Compound 7a]
Structure:

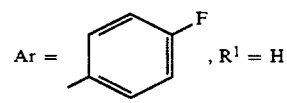

Melting point: 119–120° C.
$^1$H-NMR (CDCl$_3$): δ
1.16(s, 6H), 1.21(s, 9H), 1.31(s, 6H)
1.33(s, 9H), 2.18(t, J=5.9Hz, 1H)
2.28(t, J=5.9Hz, 1H)
3.74(d, J=5.9Hz, 2H)
3.81(d, J=5.9Hz, 2H)
6.8–6.9(m, 6H), 7.0–7.2(m, 6H)
[Compound 8a]
Structure:

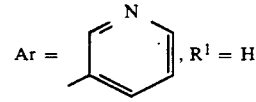

TABLE 1-continued

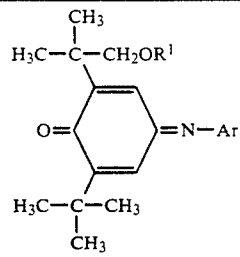

(About 1:1 mixture of syn-isomer and anti-isomer)

Properties: Oily product
$^1$H-NMR (CDCl$_3$): δ
1.16(s, 6H), 1.20(s, 9H), 1.32(s, 6H)
1.34(s, 9H), 2.25–2.45(m, 2H)
3.74(broad s, 2H), 3.83(broad s, 2H)
6.75(d, J=2.7Hz, 1H)
6.81(d, J=2.7Hz, 1H)
7.07(d, J=2.7Hz, 1H)
7.12(d, J=2.7Hz, 1H)
7.2–7.3(m, 2H), 7.3–7.4(m, 2H)
8.1–8.2(m, 2H), 8.4–8.5(m, 2H)
[Compound 9a]
Structure:

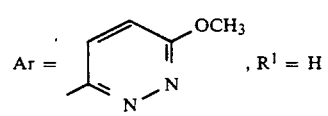

Melting point: 111–116° C.
$^1$H-NMR (CDCl$_3$): δ
1.19(s, 6H), 1.23(s, 9H), 1.31(s, 6H)
1.33(s, 9H), 2.05–2.41(m, 2H)
3.74(s, 2H), 3.81(s, 2H), 4.15(s, 3H)
4.16(s, 3H), 7.05(d, J=2.6Hz, 2H)
7.05–7.10(m, 3H)
7.14(d, J=2.6Hz, 1H)
7.25(d, J=2.0Hz, 1H)
7.29(d, J=2.0Hz, 1H)
[Compound 10a]
Structure:

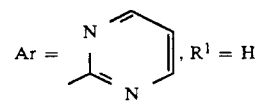

Melting point: 149.5–151° C.
$^1$H-NMR (CDCl$_3$): δ
1.14(s, 6H), 1.19(s, 9H), 1.30(s, 6H)
1.32(s, 9H), 2.15–2.31(m, 2H)
3.71(d, J=4.7Hz, 2H)
3.79(d, J=4.7Hz, 2H)
6.67(d, J=2.5Hz, 1H)
6.73(d, J=2.5Hz, 1H)
7.11(d, J=2.5Hz, 1H)
7.13(t, J=4.8Hz, 2H)
7.15(d, J=2.5Hz, 1H)
8.753(d, J=4.8Hz, 2H)
8.755(d, J=4.8Hz, 2H)
[Compound 11a]
Structure:

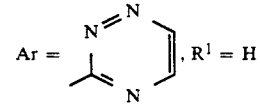

Melting point: 140.5–143° C.
$^1$H-NMR (CDCl$_3$): δ
1.16(s, 6H), 1.20(s, 9H), 1.32(s, 6H)
1.34(s, 9H), 2.05–2.21(m, 2H)
3.73(m, 2H), 3.81(m, 2H)
6.70(broad d, J=2.3Hz, 1H)

TABLE 1-continued

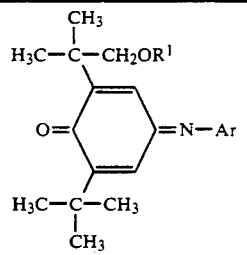

(About 1:1 mixture of syn-isomer and anti-isomer)

6.77(broad d, J=2.3Hz, 1H)
7.13(broad d, J=2.3Hz, 1H)
7.18(broad d, J=2.3Hz, 1H)
8.66(d, J=2.4Hz, 2H)
9.11(d, J=2.4Hz, 2H)

[Compound 12a]
Structure:

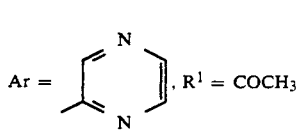

Properties: Oily product
$^1$H-NMR (CDCl$_3$): δ
1.20(s, 9H), 1.21(s, 6H), 1.33(s, 9H)
1.34(s, 6H), 1.97(s, 3H), 2.00(s, 3H)
4.26(s, 2H), 4.36(s, 2H)
6.92(d, J=2.6Hz, 2H)
7.05–7.06(m, 2H), 8.4–8.5(m, 6H)

[Compound 13a]
Structure:

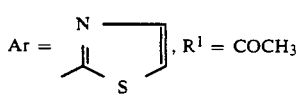

Properties: Oily product
$^1$H-NMR (CDCl$_3$): δ
1.29(s, 9H), 1.30(s, 6H), 1.31(s, 9H)
1.32(s, 6H), 1.98(s, 6H), 4.31(s, 2H)
4.35(s, 2H), 6.9–7.0(m, 2H)
7.4–7.5(m, 2H), 7.7–7.9(m, 2H)
8.04(d, J=2.5Hz, 1H)
8.06(d, J=2.5Hz, 1H)

TABLE 2

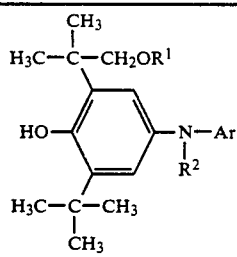

[Compound 1]
Structure:

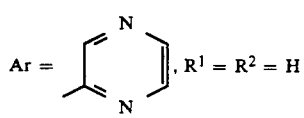

Melting point: 223.5–226° C.
$^1$H-NMR [(CD$_3$)$_2$SO]): δ
1.33(s, 6H), 1.37(s, 9H)
3.57(d, J=1.7Hz, 2H)

TABLE 2-continued

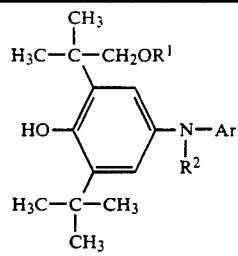

7.10(broad t, J=1.7Hz, 1H)
7.35(d, J=2.5Hz, 1H)
7.39(d, J=2.5Hz, 1H)
7.75(d, J=2.7Hz, 1H)
7.98(dd, J=2.7Hz, 1.4Hz, 1H)
8.08(d, J=1.4Hz, 1H), 8.99(s, 1H)
10.38(s, 1H)

[Compound 2]
Structure:

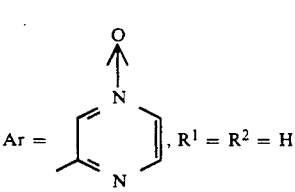

Melting point: 270–271° C.(decomposition)
$^1$H-NMR [(CD$_3$)$_2$SO]): δ
1.32(s, 6H), 1.36(s, 9H)
3.57(d, J=3.7Hz, 2H)
7.16(t, J=3.7Hz, 1H)
7.24(d, J=2.4Hz, 1H)
7.28(d, J=2.4Hz, 1H)
7.54(dd, J=4.1Hz, 1.5Hz, 1H)
7.60(d, J=1.5Hz, 1H)
7.97(d, J=4.1Hz, 1H), 9.05(s, 1H)
10.50(s, 1H)

[Compound 3]
Structure:

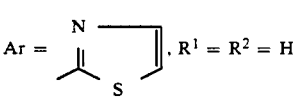

Melting point: 177.5–180.5° C.(decomposition)
$^1$H-NMR (CDCl$_3$): δ
1.41(s, 9H), 1.44(s, 6H), 3.75(s, 2H)
6.44(d, J=3.6Hz, 1H)
6.99(s, 2H), 7.11(d, J=3.6Hz, 1H)

[Compound 4]
Structure:

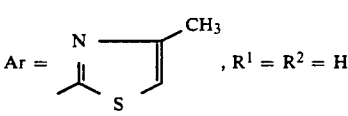

Melting point: 180–182° C.
$^1$H-NMR [(CD$_3$)$_2$SO]): δ
1.32(s, 6H), 1.35(s, 9H), 2.16(s, 3H)
3.56(s, 2H), 6.23(s, 1H)
7.10(broad s, 1H), 7.26(s, 1H)
7.30(s, 1H), 9.54(s, 1H)
10.33(broad s, 1H)

[Compound 5]
Structure:

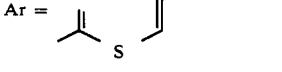

Melting point: 79–81° C.

TABLE 2-continued

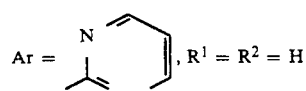

Melting point: 243-244.5° C.(decomposition)
$^1$H-NMR [(CD$_3$)$_2$SO]: δ
1.34(s, 6H), 1.37(s, 9H)
3.57(d, J=2.7Hz, 2H)
3.89(s, 3H), 6.96(d, J=9.4Hz, 1H)
7.05(d, J=9.4Hz, 1H)
7.08(t, J=2.7Hz, 1H)
7.37(d, J=2.4Hz, 1H)
7.46(d, J=2.4Hz, 1H), 8.55(s, 1H)
10.28(s, 1H)
[Compound 10]
Structure:

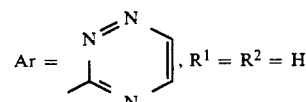

Melting point: 262.5-264.5° C.
$^1$H-NMR [(CD$_3$)$_2$SO]: δ
1.32(s, 6H), 1.36(s, 9H)
3.56(broad d, J=4.7Hz, 2H)
6.67(t, J=4.8Hz, 1H)
7.07(broad t, J=4.7Hz, 1H)
7.42(s, 2H), 8.35(d, J=4.8Hz, 2H)
9.03(s, 1H), 10.32(s, 1H)
[Compound 11]
Structure:

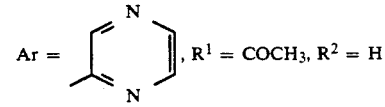

Melting point: 245.5-247.5° C.(decomposition)
$^1$H-NMR [(CD$_3$)$_2$SO]: δ
1.33(s, 6H), 1.36(s, 9H), 3.57(s, 2H)
7.16(broad s, 1H), 7.42(s, 2H)
8.33(d, J=2.2Hz, 1H)
8.66(d, J=2.2Hz, 1H), 9.60(s, 1H)
10.48(s, 1H)
[Compound 12]
Structure:

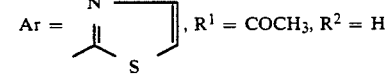

Melting point: 120-121° C.
$^1$H-NMR (CDCl$_3$): δ
1.44(s, 9H), 1.47(s, 6H), 2.06(s, 3H)
4.33(s, 2H), 6.16(s, 1H)
6.47(broad s, 1H), 7.17(d, J=2.3Hz, 1H)
7.19(d, J=2.3Hz, 1H)
7.91(d, J=2.4Hz, 1H)
8.04(broad d, J=2.4Hz, 1H)
8.09(broad s, 1H)
[Compound 13]
Structure:

$^1$H-NMR (CDCl$_3$): δ
1.29(t, J=7.1Hz, 3H), 1.40(s, 9H)
1.42(s, 6H), 3.56(s, 2H)
3.73(s, 2H), 4.20(q, J=7.1Hz, 2H)
6.27(s, 1H), 6.94(s, 2H)
[Compound 6]
Structure:

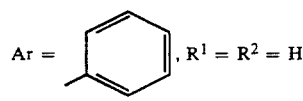

Melting point: 133-134° C.
$^1$H-NMR (CDCl$_3$): δ
1.41(s, 9H), 1.42(s, 6H)
2.51(t, J=3.1Hz, 1H)
3.80(d, J=3.1Hz, 2H)
5.44(broad s, 1H)
6.78(dd, J=7.3Hz, 7.3Hz, 1H)
6.86(d, J=8.2Hz, 2H)
6.94(d, J=2.6Hz, 1H)
7.02(d, J=2.6Hz, 1H)
7.19(dd, J=8.2Hz, 7.3Hz, 2H)
8.93(s, 1H)
[Compound 7]
Structure:

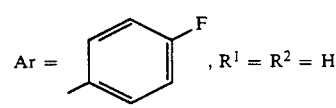

Melting point: 120-121° C.
$^1$H-NMR (CDCl$_3$): δ
1.40(s, 15H), 2.55(t, J=3.5Hz, 1H)
3.80(d, J=3.5Hz, 2H)
5.33(broad s, 1H), 6.8-7.0(m, 6H)
8.93(s, 1H)
[Compound 8]
Structure:

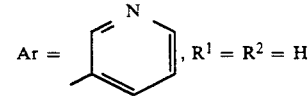

Melting point: 241.5-244.5° C.(decomposition)
$^1$H-NMR [(CD$_3$)$_2$SO]: δ
1.31(s, 6H), 1.35(s, 9H)
3.57(d, J=3.5Hz, 2H)
6.86(d, J=2.5Hz, 1H)
6.88(d, J=2.5Hz, 1H)
7.0-7.3(m, 3H)
7.84(dd, J=4.5Hz, 1.2Hz, 1H)
7.87(s, 1H), 8.16(d, J=2.7Hz, 1H)
10.39(s, 1H)
[Compound 9]
Structure:

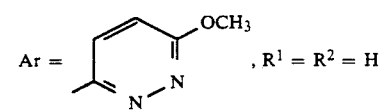

TABLE 2-continued

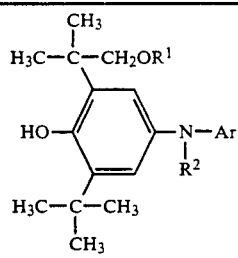

Melting point: 127-128.5° C.
$^1$H-NMR (CDCl$_3$): δ
1.44(s, 9H), 1.48(s, 6H), 2.05(s, 3H)
4.34(s, 2H), 6.08(broad, 1H)
6.52(d, J=3.7Hz, 1H)
7.16(d, J=2.6Hz, 1H)
7.18(d, J=2.6Hz, 1H)
7.23(d, J=3.7Hz, 1H)
8.30(broad, 1H)

[Compound 14]
Structure:

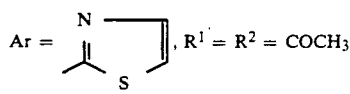, R$^1$ = R$^2$ = COCH$_3$

Melting point: 152.5-154.5° C.
$^1$H-NMR (CDCl$_3$): δ
1.45(s, 9H), 1.47(s, 6H), 2.00(s, 3H)
2.06(s, 3H), 4.32(s, 2H), 6.54(s, 1H)
7.01(d, J=3.6Hz, 1H)
7.05(d, J=2.4Hz, 1H)
7.10(d, J=2.4Hz, 1H)
7.42(d, J=3.6Hz, 1H)

[Compound 15]
Structure:

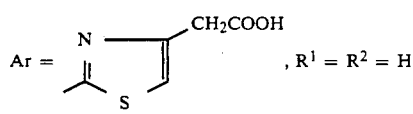, R$^1$ = R$^2$ = H

Melting point: 138-139° C.(decomposition)
$^1$H-NMR [(CD$_3$)$_2$SO]: δ
1.32(s, 6H), 1.35(s, 9H), 3.48(s, 2H)
3.56(s, 2H), 6.51(s, 1H)
7.20(broad s, 1H), 7.24(s, 1H)
7.29(s, 1H), 9.95(broad s, 1H)
10.48(s, 1H)

The pharmacological test example using the compound of the invention is described below.

PHARMACOLOGICAL TEST EXAMPLE 1

The antiinflammatory activity of the compound of the invention was determined by an air pouch technique generally conforming to the method described in the literature [Proc. Soc. Exp. Biol. Med., 82, 328-333, 1953].

The test was carried out using male Wistar rats (average body weight 200 g, 7 animals per group). A thick paper sheet with an oval cutout (2×5 cm) was attached to the clipped back of the animal under pentobarbital anesthesia. The skin was picked up through the central cutout and 10 ml of air was injected subcutaneously to prepare an air pouch. Then, 1 ml of 2% croton oil, as a phlogogenic agent, was injected into the pouch. The paper sheet was removed and the animal was gently rotated in order that the croton oil would be thoroughly contacted with the inner wall of the pouch.

The test compound suspended in 5% gum arabic was administered into the pouch (25 mg/kg/day) once a day for 6 days beginning the day after preparation of the pouch. The group of animals subjected to the above treatment was designated as the experimental group.

On day 8, the animals were bled to death and the amount (ml) of exudate in the pouch was measured. The antiinflammatory rate was calculated with the result in the control group (a group not receiving the test compound) as a reference according to the following equation.

$$\text{Antiinflammatory rate (\%)} = \frac{\text{Amount of exudate in the control group} - \text{Amount of exudate in the experimental group}}{\text{Amount of exudate in the control group}} \times 100$$

The results are shown below in Table 3.

TABLE 3

| Test compound | Antiinflammatory rate (%) |
| --- | --- |
| Compound 1 | 68** |
| Compound 3 | 71** |
| Compound 6 | 14 |
| Compound 8 | 19 |
| Compound 10 | 24* |
| Compound 11 | 20 |
| Compound 13 | 60** |
| Compound 14 | 51** |
| Compound 15 | 32** |

In the table, ** and * stand for p < 0.01 and p < 0.05, respectively.

Table 3 reveals that the compound of the invention have significant antiinflammatory activity and can be useful antiinflammatory agents.

Some formulation examples for the compounds of the invention are presented below.

| Formulation Example 1 | |
| --- | --- |
| Compound 1 (the compound of the invention as prepared in Example 1) | 250 g |
| Crystalline cellulose J.P.* | 30 g |
| Corn starch J.P. | 17 g |
| Talc J.P. | 2 g |
| Magnesium stearate J.P. | 1 g |
| Total | 300 g |

*J.P. = Listed on the Japanese Pharmacopoeia

The above components were respectively comminuted and admixed well to give a uniform composition according to the above formula. The composition was filled into gelatin capsules of the desired size for oral administration to give 1000 capsules.

| Formulation Example 2 | |
| --- | --- |
| Compound 3 (the compound of the invention as prepared in Example 3) | 100 g |
| Crystalline cellulose (trademark "Avicel pH101", Asahi Chemical Industry Co., Ltd.) | 40 g |
| Corn starch | 30 g |
| Magnesium stearate | 2 g |
| Total | 172 g |
| Hydroxypropylmethylcellulose (trademark "TC-5", Shin-Etsu Chemical Co., Ltd.) | 8.0 g |
| Polyethylene glycol 6000 | 2.4 g |
| Color | 0.6 g |
| Titanium dioxide | 4.0 g |
| Water | 85.0 g |

| Formulation Example 2 | |
|---|---|
| Total | 100 g |

Compound 3, crystalline cellulose, corn starch and magnesium stearate were taken and milled together and the composition was compression-molded with a dragee R 8 mm punch. The resultant tablets were coated with a film-coating composition consisting of hydroxypropylmethylcellulose (TC-5), polyethylene glycol 6000, color, titanium dioxide and water to give film-coated tablets meeting the above formula.

| Formulation Example 3 | |
|---|---|
| Compound 14 (the compound of the invention as prepared in Example 14) | 2 g |
| Purified lanolin | 5 g |
| Bleached beeswax | 5 g |
| White petrolatum | 88 g |
| Total | 100 g |

Bleached beeswax was melted by warming and thereto were added compound 14, purified lanolin and white petrolatum. The mixture was warmed until a liquid consistency was obtained and, then, stirred until it solidified, giving an ointment of the above formula.

We claim:

1. A p-aminophenol derivative of the formula

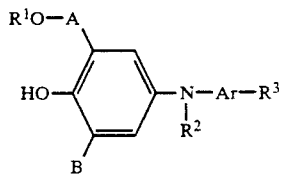

wherein each of $R^1$ and $R^2$ is independently a hydrogen atom or a $C_{1-6}$ acyl group; Ar is a pyrazine ring; $R^3$ is a hydrogen atom, a $C_{1-6}$ alkyl group, a $C_{1-6}$ alkyl group, a $C_{1-6}$ alkoxy-carbonyl-$C_{1-6}$ alkyl group, a $C_{1-6}$ alkoxy group, a halogen atom or a carboxy-$C_{1-6}$ alkyl group; A is a $C_{1-6}$ alkylene group; and B is a $C_{1-6}$ alkyl group, or a salt thereof.

2. A 4-imino-2,5-cyclohexadien-1-on derivative of the formula

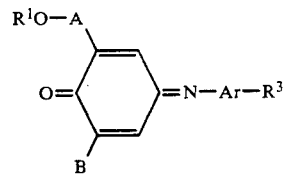

wherein $R^1$ is a hydrogen atom or a $C_{1-6}$ acyl group; Ar is a pyrazine ring; $R^3$ is a hydrogen atom, a $C_{1-6}$ alkyl group, a $C_{1-6}$ alkoxycarbonyl-$C_{1-6}$ alky group, a $C_{1-6}$ alkoxy group, a halogen atom or a carboxy-$C_{1-6}$ alkyl group; A is a $C_{1-6}$ alkylene group; and B is a $C_{1-6}$ alkyl group, or a salt thereof.

3. The compound as defined in clam 1 which has the formula

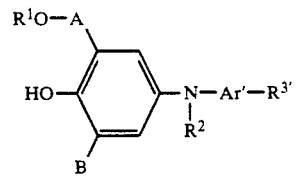

wherein $R^1$, $R^2$, A and B are as defined in claim 1; Ar' is a pyrazine ring; and $R^{3'}$ is a hydrogen atom.

4. The compound as defined in claim 3 which is 2-(1,1-dimethylethyl)-6-(1,1-dimethyl-2-hydroxyethyl)-4-pyrazinylaminophenol.

5. An anti-inflammatory composition comprising an anti-inflammation effective amount of the compound defined in claim 1 or a pharmaceutically acceptable salt thereof in combination with a pharmaceutically acceptable carrier or excipient.

6. A method for treating inflammation in a patient, comprising administering to the patient an anti-inflammation effective amount of the compound defined in claim 1 or a pharmaceutically acceptable salt thereof.

* * * * *